United States Patent [19]

Huber

[11] 4,416,736
[45] * Nov. 22, 1983

[54] PROCEDURE FOR THE ENRICHMENT OF THE ELEMENT OF INTEREST FROM A SOLUTION FOR NONFLAME ATOMIC ABSORPTION SPECTROSCOPY

[75] Inventor: Bernhard Huber, Überlingen, Fed. Rep. of Germany

[73] Assignee: Bodenseewerk Perkin-Elmer & Co., GmbH, Überlingen, Fed. Rep. of Germany

[*] Notice: The portion of the term of this patent subsequent to Oct. 20, 1998 has been disclaimed.

[21] Appl. No.: 223,070

[22] Filed: Jan. 6, 1981

[30] Foreign Application Priority Data

Jan. 8, 1980 [DE] Fed. Rep. of Germany ....... 3000446

[51] Int. Cl.$^3$ ............................................. G01N 27/46
[52] U.S. Cl. ................................. 204/1 T; 73/864.81; 204/406; 204/412; 204/434; 324/71.1; 324/439; 356/36; 356/312; 422/80; 436/150; 436/155
[58] Field of Search ................. 204/1 T, 195 R, 400, 204/412, 434; 356/312, 36; 73/864.11, 864.12, 864.81; 23/230 PC; 324/439, 71 R, 71.1; 436/150, 155

[56] References Cited

U.S. PATENT DOCUMENTS

| | | | |
|---|---|---|---|
| 3,267,364 | 8/1966 | Page et al. | 204/195 R |
| 3,293,155 | 12/1966 | Stone | 204/290 R |
| 3,356,597 | 12/1967 | Schmidt | 204/195 R |
| 3,662,604 | 5/1972 | Low et al. | 73/864.34 |
| 3,671,129 | 6/1972 | Wiedeking | 356/312 |
| 3,681,212 | 8/1972 | McKissick | 204/45 R |
| 3,684,679 | 8/1972 | Smith et al. | 204/195 C |
| 3,719,884 | 3/1973 | Laroche | 204/1 T |
| 3,824,016 | 7/1974 | Woodriff et al. | 356/312 |
| 3,912,613 | 10/1975 | Heuser | 204/195 R |
| 3,943,043 | 3/1976 | Billington et al. | 204/195 R |
| 4,111,051 | 9/1978 | Tamm et al. | 73/864.12 |
| 4,295,854 | 10/1981 | Huber | 23/230 PC |

OTHER PUBLICATIONS

"Coupling of Pre-Electrolysis . . . Absorption Spectrometry . . . ", by G. Torsi, Annali di Chimica, 67/1977, pp. 557-566.

Primary Examiner—T. Tung
Attorney, Agent, or Firm—S. A. Giarratana; F. L. Masselle; R. A. Hays

[57] ABSTRACT

An apparatus for enriching a sought element from a solution for flameless atomic absorption spectroscopy includes a constant voltage current source. The solution is enriched by electrodepositing the sought element therefrom and integrating the current with respect to time.

8 Claims, 1 Drawing Figure

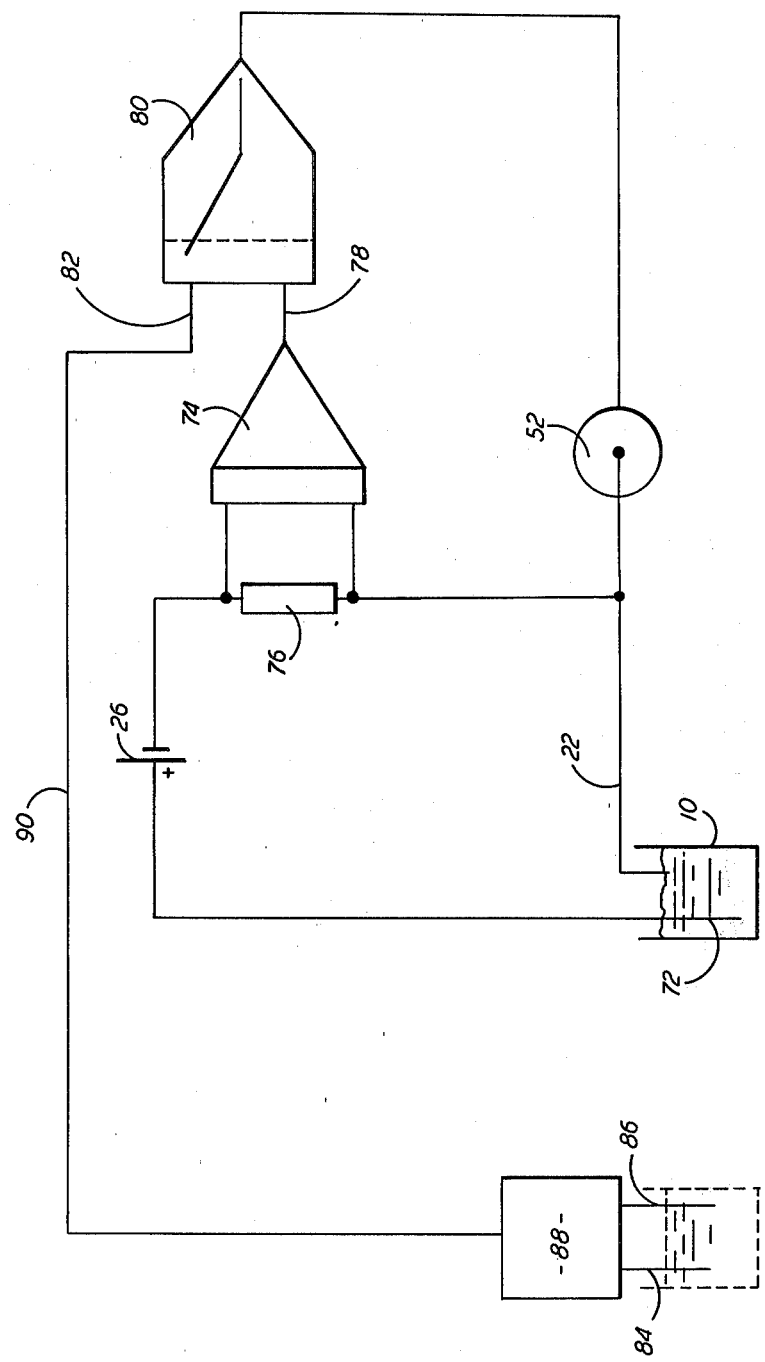

PROCEDURE FOR THE ENRICHMENT OF THE ELEMENT OF INTEREST FROM A SOLUTION FOR NONFLAME ATOMIC ABSORPTION SPECTROSCOPY

The invention relates to a method for enriching an element looked for from a solution for flameless atomic absorption spectroscopy.

Such a method is the subject of the Main Patent (patent application No. P 29 03 246.0-52) U.S. Pat. No. 4,295,854.

It is essential that the amount of the element sought which is deposited at the electrode is in a defined relationship to the concentration of the element in the solution. The quantity of the element sought which is being deposited within a predetermined current time integral (ampere seconds) is highly dependent on which other elements are contained additionally in the solution, on relative mobilities of the different ions and on nonuniformities in the distribution of the ions through the sample vessel which may develop during electrolysis.

For this reason the solution is stirred in the sample vessel during electrolysis to always ensure uniform ion distribution. Additionally, after measuring the atomic absorption a predetermined amount of the substance sought is added and thereafter the electrolysis and the atomic absorption measurement are repeated in cases in which the composition of the sample is unknown with regard to those components contained in the sample in addition to the element sought. By this "addition method" standardization is obtained from which the relationship between the amount of the element sought which has been deposited at the electrode and the concentration thereof in the solution can be determined.

It has turned out that, additionally, the deposited amount of the element sought depends on the way the current is passed through the solution during electrolysis. If the electrolysis is conducted at constant voltage, variations in current will occur due to changes in the resistance of the electrolysis apparatus. With a predetermined duration of electrolysis this will imply a variation in the total deposited amount of the metal since the amount thereof deposited is proportional to the product of current and time. If the operation is at constant current, the voltage supplied at the electrodes and therewith the electric field strength between the electrodes will vary in the case of resistance changes. This will affect ionic mobilities so that more ions of the element sought will reach the electrode at a higher voltage.

Changes in resistance may be caused, for instance, by gas bubbles of, say, hydrogen which form at the electrode and stay there over shorter or longer periods of time. By such gas bubbles the transfer resistance between the solution and the electrode is changed.

Changes in between one measurement and the next following, also, may be caused by changes in geometry, for instance by variations in the immersion depth of the electrode in the solution or in the liquid level of the solution in the sample vessel.

It is the object of the invention to deposit the element sought at the electrode in an amount which is unaffected by such effects and which is uniquely dependent on its concentration in the solution.

According to the invention this object is achieved at least in part by the measures as given in the characterizing clause of patent claim 1.

According to the invention the method operates at a constant voltage between the electrodes so that a constant field strength will result. The electrolysis is conducted until a predetermined current time integral is reached to which a predetermined total amount of deposited ions corresponds. It has been shown that under such conditions a predominantly unique relationship exists of the amount of the element sought which is deposited at the electrode to the concentration thereof in the solution.

If the composition of the solution is unknown in respect of the other (matrix) components contained therein, standardization can be obtained by adding a known quantity of the element sought to the solution to be investigated and carrying out another electrolysis and measurement as already suggested in the Main Patent.

Further developments of the method according to the invention as well as an apparatus for carrying out the method are the subject of the subclaims.

An embodiment of the invention is illustrated hereinbelow with reference to the associated drawing showing schematically an apparatus for carrying out the method according to the invention.

The mechanical structure of the apparatus may correspond substantially to the apparatus according to the Main Patent which is incorporated herein by reference and parts thereof corresponding thereto are assigned the same reference numerals.

A sample vessel is designated by 10, a first electrode 22 made of electrically conductive material resistant to high temperatures being adapted for immersion thereinto. This is achieved by means of an actuating mechanism including a servo motor 52 and retaining the electrode 22 in an insulating fashion by means of which mechanism the electrode 22 may be moved into the sample vessel 10 and out of the same into the sample introduction port of a graphite tube (not shown). A second electrode 72 is immersed into the solution forming the sample liquid and is in electrically conducting contact therewith. First electrode 22 is connected to the negative terminal of a current source 26 forming a constant voltage source, the second electrode 72 being connected to the other, positive, terminal current source 26. An integrator 74 is provided to temporally integrate the current flowing through electrodes 22 and 72. Furthermore, means are provided for interrupting the electrolysis after a predetermined output signal has been reached at the integrator 74. Preferably, the electrolysis is interrupted in such a way that the actuating mechanism including servo motor 52 is designed to be energized for withdrawing the first electrode 22 from the solution once the output signal of integrator 74 has reached said predetermined level.

In detail, a low-resistance precision resistor for measuring purposes 76 is connected within the circuit including electrodes 22, 72. The integrator 74 is a voltage integrator connected to said resistor. The output signal from integrator 74 is supplied to a first input 78 of a comparator 80 to the second input 82 of which a reference signal representing said predetermined value is fed. The servo motor 52 of the actuating mechanism is controlled by the output signal from comparator 80.

A pair of auxiliary electrodes 84, 86 is adapted to be immersed into sample vessel 10. The auxiliary electrodes are connected to a device 88 for determining the electric resistance of the solution between the auxiliary electrodes and for generating a signal proportional to the reciprocal of said resistance. Means 90 are provided to feed said signal to the second input 82 of comparator 80 as a reference signal so that said predetermined value will be proportional to the conductivity of the solution. The auxiliary electrodes 84 and 86 are adapted for being withdrawn from the sample vessel 10 before the electrolysis is carried out. Device 88 includes means to store the signal proportional to the reciprocal of the resistance so that said signal will be available as a reference signal even after the auxiliary electrodes 84, 86 have been withdrawn. Preferably the auxiliary electrodes are platinum electrodes. To avoid polarisation effects, an a.c. voltage is fed to the auxiliary electrodes.

Enrichment of an element sought from a solution for flameless atomic absorption spectroscopy is obtained with the apparatus as described in the following manner:

Electrode 22 is introduced outside of the atomic absorption spectrometer into sample vessel 10 containing the solution. An electric d.c. current is passed through the solution via electrode 22 so that components of the solution including the element sought become deposited at electrode 22. By means of servo motor 52 the electrode 22 is removed from the sample vessel and introduced into a graphite tube (not shown) through which the measuring light beam of the atomic absorption spectrometer passes. The graphite tube, then, is heated whereby the electrode 22 is heated, too, indirectly and whereby the sample components deposited thereon become atomized.

By using a constant voltage source for the current source 26 in the apparatus as described the voltage between the electrode 22 and counterelectrode 72 is kept constant. The current passing through the solution via electrodes 22, 72 is integrated with time by means of integrator 74 in connection with precision resistor 76. When the current time integral as represented by the signal applied to the input 82 of comparator 80 reaches a predetermined level, the electrolysis is interrupted. Therefor, the first electrode 22 is withdrawn from the solution. Instead, the current passing through the electrodes could have been switched off. In some cases, however, this would have the disadvantage that portions of the deposited metal could become re-dissolved.

By means of platinum electrodes 84, 86 and the a.c. current the conductivity of the solution is being measured. Said predetermined level of the current time integral, then, is selected so as to be proportional to the conductivity thus measured.

Assuming that the element sought is present in the solution only at a low concentration and practically does not contribute to the conductivity of the solution, which will be the case in general for elements to be determined by atomic absorption spectroscopy, then the conductivity measurement will yield a measure of the current passed through the solution by the matrix during electrolysis. The element sought contributes to this current by a (negligible) proportion depending on its concentration in the solution. The higher the conductivity of the solution and thus the current caused substantially by the matrix, the longer the current will have to flow to deposit the same amount of the element sought at the electrode at a predetermined concentration thereof.

This is being accounted for by making the predetermined current time integral at which the electrolysis will be interrupted proportional to the solution conductivity. In case that deposition of the element sought at the electrode is not affected by secondary effects originating from the matrix composition but is affected by the distribution of the current over the different ions present in the solution, then a unique relationship of the deposited amount of the element sought can be established to its concentration in the solution even without standardizing measurements in accordance with the "addition method".

I claim:

1. Method for enriching a sought element from a solution for flameless atomic absorption spectroscopy, said method comprising the following steps:

inserting an electrode into a sample vessel containing said solution, said vessel being outside an atomic absorption spectrometer;

maintaining a constant voltage between said electrode and a counterelectrode;

integrating, with respect to time, the current passing through said solution via said electrodes;

terminating the electrolysis when a predetermined value of the current time integral has been reached;

removing said electrode from said sample vessel and inserting said electrode into a graphite tube through which the measuring light beam of said atomic absorption spectrometer passes; and heating said graphite tube, whereby said electrode is indirectly heated and said sample components deposited thereon are atomized.

2. Method as claimed in claim 1 including the further step of:

measuring the conductivity of said solution using platinum electrodes and an a.c. current and said predetermined current time integral in the electrolysis is selected to be proportional to the conductivity thus measured.

3. Apparatus useful for enriching a sought element from a solution for flameless atomic absorption spectroscopy, said apparatus comprising:

a graphite tube atomizer including a graphite tube having a sample introduction port therein;

a sample vessel;

a current source, said current source being a constant voltage source;

a first electrode made of electrically conductive material resistant to high temperatures and connected to one terminal of said current source;

an actuating mechanism, in which said first electrode is insulatingly retained, by means of which said first electrode is adapted to be moved into said sample vessel and out of same into said sample introduction port of said graphite tube;

a counterelectrode connected to the other terminal of said current source and placed in electrically conducting contact with said sample;

an integrator for temporally integrating the current passing through said first and said second electrode; and means for interrupting the electrolysis when a predetermined output signal of said integrator has been reached.

4. Apparatus as claimed in claim 3 wherein said actuating mechanism is adapted to withdraw said first electrode from said solution when the output signal of said integrator has reached said predetermined value.

5. Apparatus as claimed in claim 4, wherein:

a precision resistor for measuring purposes is connected in the current circuit of said electrodes;

said integrator is a voltage integrator connected to said precision resistor, the output signal from said integrator being supplied to a first input of a comparator to the second input of which a reference signal representing said predetermined value is provided; and a servomotor of said actuating mechanism being controlled by the output signal from said comparator.

6. Apparatus as claimed in claim 5, further comprising:

a pair of auxiliary electrodes adapted to be immersed into said sample vessel;

means for determining the electrical resistance of said solution between said auxiliary electrodes and for generating a signal proportional to the reciprocal of said resistance; and means for supplying said signal as a reference signal to said second input of said comparator so that said predetermined value becomes proportional to said solution conductivity.

7. Apparatus as claimed in claim 6, wherein:

said auxiliary electrodes are adapted to be removed from said sample vessel prior to said electrolysis; and means for storing said signal proportional to the reciprocal of the resistance and to have said signal available as a reference signal after removal of the auxiliary electrodes.

8. Apparatus as claimed in claim 7 wherein:

said voltage source, being an a.c. voltage source, is applied to said auxiliary electrodes.

* * * * *